(12) United States Patent
McMillan

(10) Patent No.: US 6,899,720 B1
(45) Date of Patent: May 31, 2005

(54) TOURNIQUET

(75) Inventor: William M. McMillan, Temecula, CA (US)

(73) Assignee: Diane C. McMillan, Temecula, CA (US)

( * ) Notice: Subject to any disclaimer, the term of this patent is extended or adjusted under 35 U.S.C. 154(b) by 493 days.

(21) Appl. No.: 10/021,876

(22) Filed: Dec. 14, 2001

Related U.S. Application Data

(60) Provisional application No. 60/255,973, filed on Dec. 14, 2000.

(51) Int. Cl.[7] .............................................. A61B 17/00
(52) U.S. Cl. ..................................................... 606/203
(58) Field of Search ................................ 606/201–204; 602/5, 19; 128/876, 878; 2/338; 24/68 R, 70 ST, 69 ST, 68 E, 115 H, 302, 170

(56) References Cited

U.S. PATENT DOCUMENTS

| 2,480,430 A | * | 8/1949 | Walters | 606/203 |
| 4,172,453 A | * | 10/1979 | Leckie | 128/878 |
| 6,053,169 A | * | 4/2000 | Hunt | 128/876 |

* cited by examiner

*Primary Examiner*—(Jackie) Tan-Uyen T. Ho
(74) *Attorney, Agent, or Firm*—Rod D. Baker; Peacock, Myers & Adams, PC

(57) ABSTRACT

A tourniquet for use in constricting blood flow to limbs. The tourniquet comprises a strap with integral pocket-assemblies, a rod, and a cam-type buckle for fixing an initial circumference. The pocket assemblies receive the ends of the rod to hold the strap in a twisted configuration after tightening with the rod.

13 Claims, 5 Drawing Sheets

TOURNIQUET

CROSS-REFERENCE TO RELATED APPLICATIONS

This application claims the benefit of the filing of U.S. Provisional Patent Application Ser. No. 60/255,973, entitled "Tourniquet", filed on Dec. 14, 2000, and the specification thereof is incorporated herein by reference.

BACKGROUND OF THE INVENTION

1. Field of the Invention (Technical Field)

The present invention relates to medical tourniquets, specifically to a medical tourniquet that is easy to use reliably and quickly.

2. Background Art

Tourniquets are used in medical emergencies to arrest life-threatening arterial or venous bleeding. A tourniquet is applied around an arm or leg, or other body extremity, to constrict the blood vessels between the patient's heart and the bleeding wound. Tourniquets must be used with care and knowledge, as stopping the flow of blood to the wound also stops the flow of blood to the entire extremity below the tourniquet; prolonged blood deprivation from improperly extended or regulated tourniquet use can lead to tissue death in the affected limb.

Because misuse of a tourniquet can be unnecessarily hazardous, properly applied direct pressure to the wound may be preferred to tourniquet use. Nevertheless, recent studies have confirmed the utility of tourniquets as the first line of medical intervention in extreme trauma situations. While proper training in proper tourniquet use remains essential, the tourniquet is receiving renewed interest as an effective tool in first-aid and paramedical treatment of severe bleeding.

Conventional tourniquets commonly in use have remained essentially unchanged for decades. Existing tourniquets typically consist of a single strap, possibly with a buckle for securing it in an adjustable loop, and a rigid rod. The looped strap is wrapped around the affected limb, and the rod is inserted between the limb and strap and then rotated, in a plane about parallel to the surface of the limb, in an "over-under" manner about the strap to twist the strap. As the strap is twisted with the rod, the effective length of the looped strap is shortened to constrict the limb. When the tourniquet is adequately tightened, the user must then temporarily secure the rod in position to maintain the twist in the strap. A variety of methods have been devised or improvised to so secure the rod, such as tucking an end of the rod back under the strap, or tying an end of the rod to the strap with a separate ribbon or cord. Known methods for securing the rod to maintain the strap constriction are generally unreliable and time consuming.

Tourniquets are commonly included, for example, in military field medical kits. The tourniquet in the U.S. military's current inventory is inadequate in its design. The tourniquet in the U.S. military inventory has remained essentially unchanged for about 50 years. When first designed, the military tourniquet was intended as a tool of last resort. Since then however, professional opinions about the utility and advantages of tourniquet use in severe cases have changed. The desirability of employing a tourniquet has increased, without any improvement to the tourniquet tools themselves. The buckle used to secure the strap on military tourniquets operates on a spring action. If the buckle is accidentally bumped, it may spring loose. Since these buckles are unreliable and unstable, they may jeopardize a briefly unattended patients life. Further, the strap itself demands the use of brute strength to achieve adequate constriction to properly restrict blood flow. Many persons using current tourniquet models are unable to tighten the tourniquet enough to occlude both arterial blood flow and venous return, creating a medical hazard.

As a resulted, a strong need remains for a tourniquet that is easy to use rapidly in emergency situations, including under conditions of darkness, and yet is reliably secured after tightening in order to prevent accidental release.

SUMMARY OF THE INVENTION (DISCLOSURE OF THE INVENTION)

The present invention relates to a tourniquet that can be applied to an affected limb rapidly and tightly enough to restrict arterial and venous blood flow. The present tourniquet apparatus is made of materials impervious to environmental conditions. The invention is simply applied, resistant to dry rot, and can be used in all weather and field conditions. The apparatus of the present invention can be applied more tightly than current tourniquets, especially those used by the military. The apparatus is simple, making it very easy to use by virtually anyone. Once tightened, the tourniquet is very secure, due to incorporation of a cam buckle to secure the strap, and special loops and pockets for securing the tightening rod. The invention finds particular utility in military applications, as well as use by, for example, outdoorsmen (e.g., hunters and fishermen), firemen, emergency medical technicians, veterinarians, and park and forest rangers.

A primary object of the present invention is to provide a tourniquet apparatus that is simple and easy to use.

A primary advantage of the present invention is that once tightened, the tourniquet apparatus reliably remains in proper tightened position, even when inadvertently bumped or jostled by patient movement.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in this disclosure.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

The tourniquet apparatus of the invention is simple in construct and use, but marks a significant improvement over existing tourniquets commonly in use.

Figure 1:
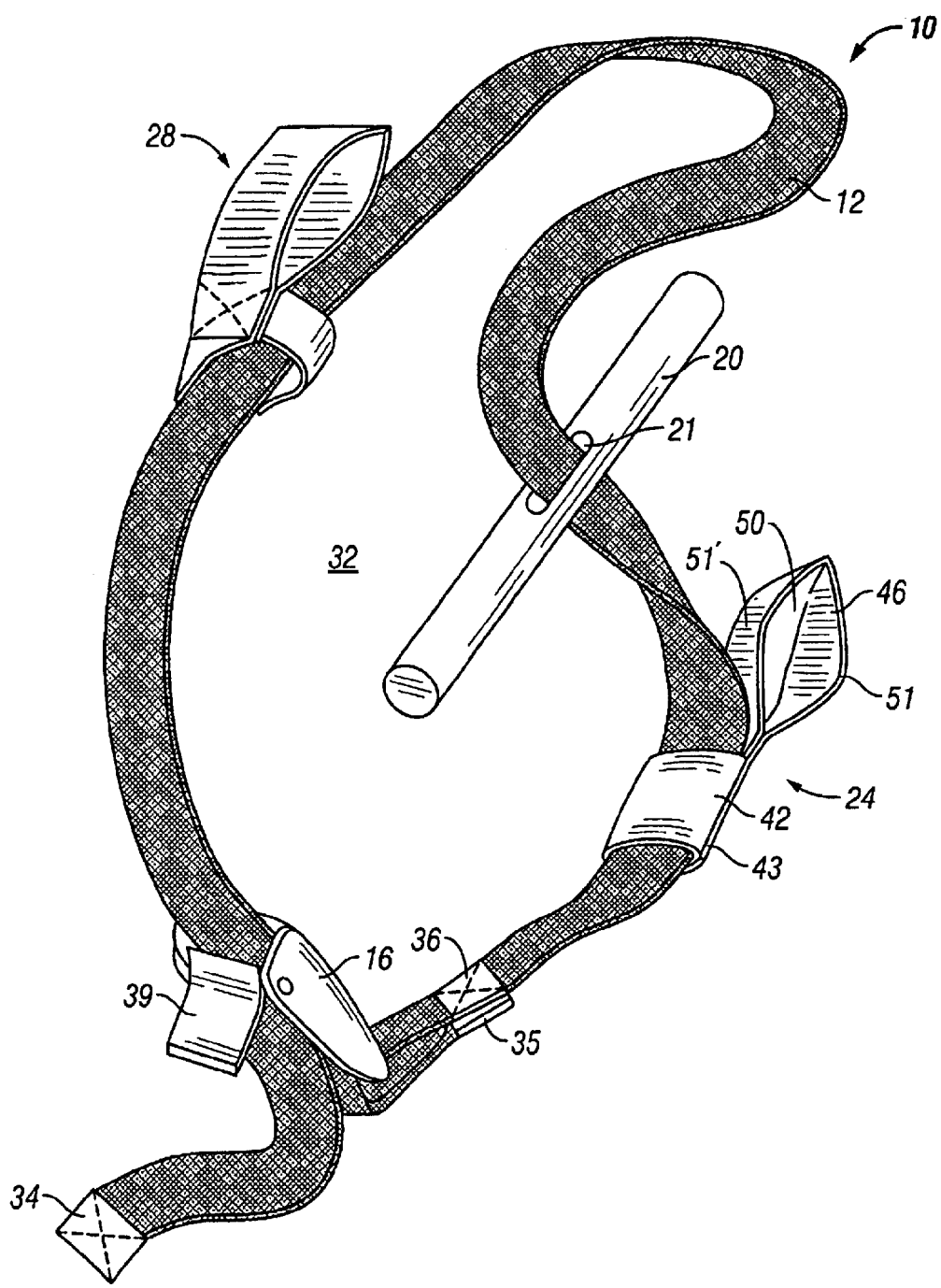
FIG. 1 is a perspective view of a preferred embodiment of the tourniquet according to the present invention.

Reference is made to FIG. 1. Tourniquet 10 of the invention features five principle components: strap 12, cam buckle 16, tightening rod 20, and two essentially identical loop-pocket assemblies 24, 28. Strap 12 performs the function of conventional tourniquets, as it is looped around the patient's affected limb or extremity and tightened to constrict the flow of blood. Strap 12 is preferably made from generally non-stretchable nylon webbing strap material, such as 1-inch woven nylon strap. Strap 12 has an overall length, before being looped and sewn according to the invention, of about preferably 28 inches to about 36 inches, although it is immediately realized that the strap can be manufactured to any suitable length, including great lengths permitting the tourniquet to be used about the thigh of larger adults (e.g., a length preferably between approximately 36 inches and approximately 40 Inches) or relatively small versions for use, for example, on children or around an adult wrist (e.g., a length preferably between approximately 6 inches and approximately 28 inches).

The ends of strap 12 are finished for durability by being doubled back and sewn into reinforced end portions 34, 35. FIG. 1 depicts strap 12 disposed into a looped configuration to define opening 32 through which the affected limb is passed prior to tightening of tourniquet 10. Strap 12 is connected to cam-type buckle 16 which is preferably manufactured from high-impact lightweight plastic, however, other suitable materials, such as metal alloys, may be utilized. One end 35 of strap 12 is looped through the rung of buckle 16 and is then doubled back against the body of the strap and preferably permanently sewn together at connection point 36. Opposing end 34 of strap 12 passes through the cam portion of buckle 16 and is adjustably movable therethrough for adjustment of the size of opening 32 defined by strap 12 to loosen or tighten tourniquet 10.

Buckle 16, which is preferably a typical "off-the-shelf" type buckle presents the advantage of allowing tourniquet 10 to be used quickly and easily, even in poor lighting conditions. The buckle is preferably a cam-type buckle, but other suitable buckles may be used. Buckle handle tab 39 is movable between a closed position and an open position. In the closed position, strap 12 is securely clamped within buckle 16 so that the length of strap 12 between free end 34 and buckle 10 is fixed. In the open position, buckle 16 is free to slidably move along strap 12 allowing the circumference of the looped tourniquet to be adjustable, and as a result, allowing the size of opening 32 to be adjustable. When tourniquet 10 is in use around a patients limb, the user pops buckle 16 into the open position and then slides buckle 16 along strap 12 cinching strap 12 to the appropriate tightness around the limb (i.e., adjusting the size of opening 32 to the proper dimension). With looped strap 12 appropriately tightened, the user can then depress buckle handle tab 39 to actuate the buckle cam to securely clamp buckle 16 on strap 12 and thus reliably and securely fix tourniquet 10 in place.

Disposed upon strap 12 is rigid cylindrical tightening rod 20. Tightening rod 20 preferably is crafted from black Delrin® composite, about 4 to about 5 inches long and about 1%-inch in diameter. Alternatively, it may be an aluminum cylinder, however, other suitable materials (e.g., wood, plastic, rubber, and other metal alloys) and dimensions (e.g., smaller or larger) for the rod may be utilized, including rods with grippers such as rubber grips disposed on the rod or indentations for receipt of fingers. Advantageously, tightening rod 20 is preferably slidably mounted upon strap 12 (depicted in FIG. 1), by passing the strap through a correspondingly sized and medially located aperture 21 through the rod. The aperture 21 may be, for example, about one inch longitudinal dimension and about ⅛ inch transverse, with ends finished with a ⅛ inch diameter corner. By this means, rod 20 is fixably located upon strap 12, and is preferably never separated therefrom. However, other embodiments utilizing a removable rod that is temporarily fixable along the strap are within the scope of the invention. After being passed through aperture 21 and the cam portion of buckle 16 during initial assembly of the tourniquet, free end 34 of strap 12 may be doubled over and sewn (or otherwise fixably secured), so as to comprise a "stopper" of sufficient thickness to prevent free end 34 from passing back through either buckle 16 or aperture 21 in rod 20. Entire tourniquet 10, including loop-pocket assemblies 24, 28, can be secured as a single unit, eliminating the possibility of lost parts (if secured in such a manner). As rod 20 is slidably movable along the length of looped strap 12, it can readily be positioned by the user for use. However, the invention is advantageous in that if the user happens to drop the rod in the hurry of the moment, it will not fall to the ground and become lost or contaminated, but instead remains upon strap 12. Once positioned, rod 20 is rotated around itself (i.e., the ends of the rod are rotated around the rod's center point) to twist strap 12 thereby tightening it to constrict blood flow in the affected limb.

Key components of the invention are loop-pocket assemblies 24, 28. Loop-pocket assemblies 24, 28, are essentially identical. The preferred embodiment of the invention features a pair of loop-pocket assemblies, although a workable embodiment may feature a single loop-pocket assembly. Each assembly 24, 28 is preferably manufactured from 1-inch non-stretchable woven nylon web strapping. Referring collectively to FIGS. 1 and 4A–D, each assembly 24, 28 includes looped portion 42, preferably comprised of a section of webbing configured to define a loop having approximately a 1-inch diameter. Loop portion 42 is sewn to, or otherwise permanently looped through, layers of stem 43 which is preferably comprised of three layers of webbing sewn together. The sections of nylon webbing comprising stem 43 extend outwardly to define the pocket portion, which has two pockets 45, 46 defined therein.

Figure 4A:
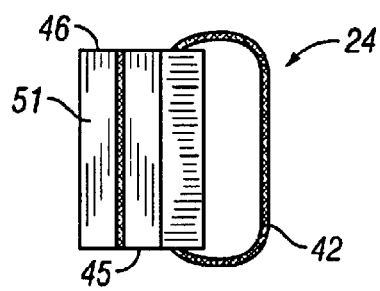
FIG. 4A is an end view of the retainer loop-pocket assembly of the invention.
Figure 4B:
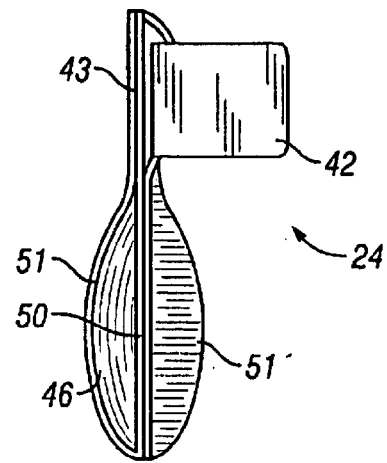
FIG. 4B is a bottom view of the loop-pocket assembly depicted in FIG. 4A.
Figure 4C:
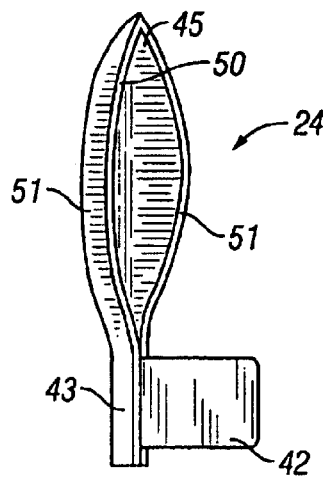
FIG. 4C is a top view of the assembly depicted in FIG. 4B.
Figure 4D:
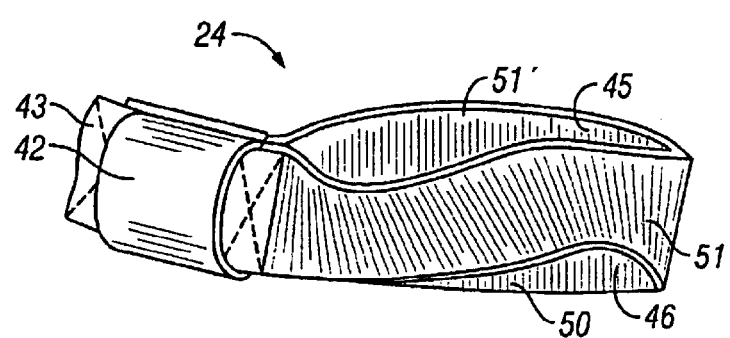
FIG. 4D is a perspective side view of the assembly depicted in FIG. 4C.

Referencing FIGS. 4A–D, pockets 45, 46 are preferably defined by three layers of webbing which are aligned in a parallel manner with one middle section 50 sandwiched between two exterior sections 51, 51'. (A single length of webbing strap may be twice doubled back upon itself to define the three layers or sections.) Two layers (one outside section 51 and middle section 50) are sewn, permanently glued, or otherwise suitably fixed along their aligned "top" edges to define first downwardly-opening pocket 46. The other sections (i.e., the other outside section and the middle section) are sewn or glued together along their aligned "bottom" edges, thereby defining second upwardly-opening pocket 45. Thus middle section 50 acts as the common wall separating two pockets 45, 46. As best depicted perhaps, in FIGS. 4B–D, pockets 45, 46 preferably open in opposite directions, thereby enhancing the versatility of the invention. FIG. 4D depicts a side view of assembly 24, showing two exterior sections or layers 51, 51', separated by middle section 50, thereby defining first pocket 46 and second pocket 45.

FIG. 1 also depicts the preferred embodiment of the present invention whereby loop-pocket assemblies 24, 28 are slidably disposed upon strap 12 by simply passing strap 12 through loop portion 42 of each respective loop-pocket assembly 24, 28. Thus, the positions of loop-pocket assemblies 24, 28 upon strap 12 are adjustably slidable by simply sliding the assemblies 24, 28 along strap 12.

Figure 2:
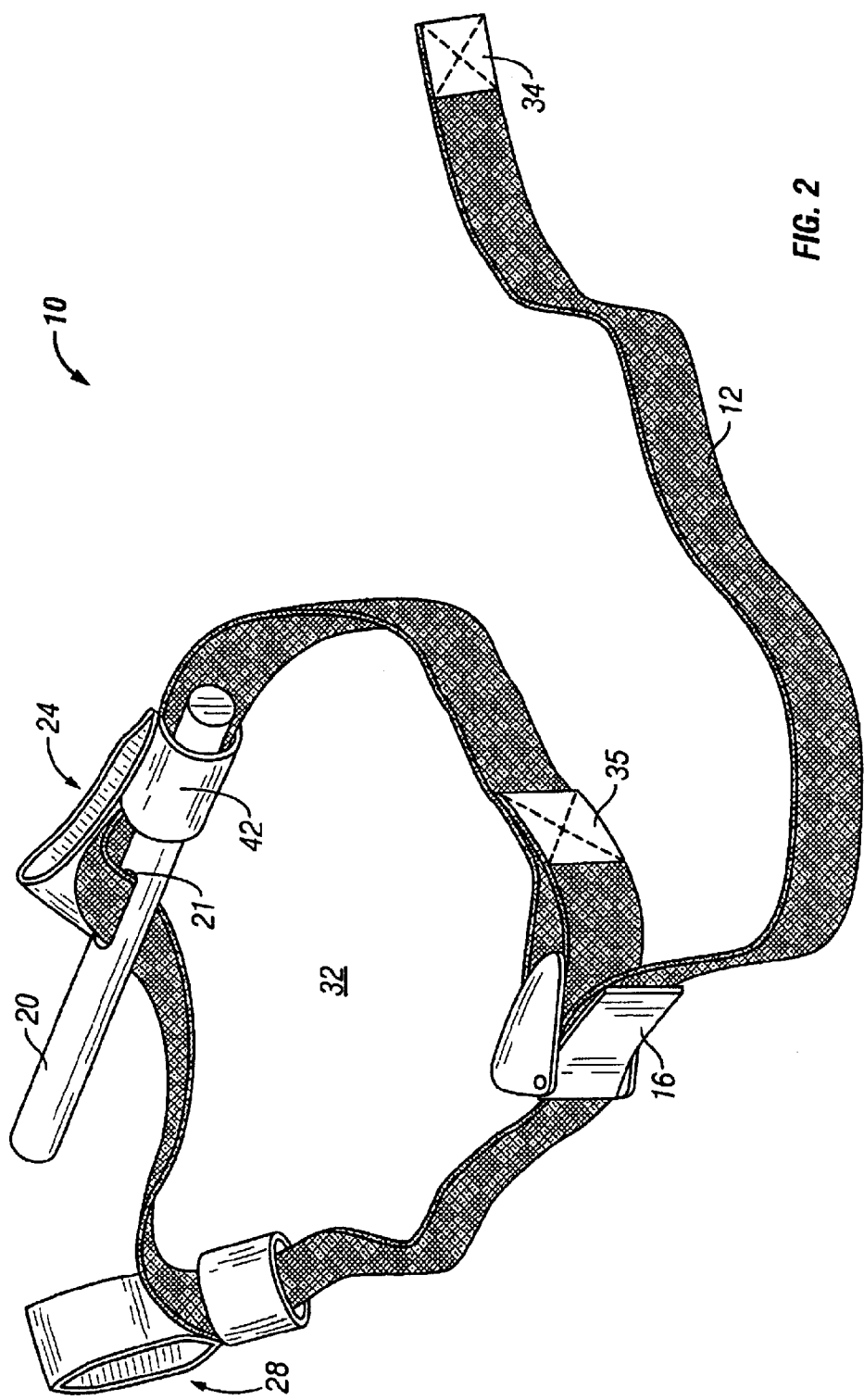
FIG. 2 is a perspective view of the apparatus of the invention depicted in FIG. 1, showing one end of the tightening rod secured in position in a retainer loop portion of a loop-pocket assembly slidably disposed upon the strap.

A principal advantage of the invention is the use of loop-pocket assemblies 24, 28 to secure tightening rod 20 in position after it is used to tighten strap 12. Attention is invited to FIG. 2, where in a preferred embodiment after rod 20 has been used to twist strap 12 to the proper tightness about the patient's limb, rod 20 is roughly parallel to tightened strap 12. (For the sake of clarity, neither the patent's limb nor the actual twisting of the strap are shown in FIG. 2; however, the nature of strap twisting and the disposition of the limb through opening 32 in the looped strap are readily understood and envisioned by one of ordinary skill in the art.) End of rod 20 may then be inserted into looped portion 42 of loop-pocket assembly 24. Rod 20 thus is held and maintained in position to secure strap 12 in the appropriately twisted condition thereby sustaining constriction upon the treated limb. FIG. 2 shows only one end of the rod held within loop 42 of one loop-pocket assembly 24. It is immediately apparent, however, that the other end of rod 20 could also be inserted into other loop portion 42 of other loop-pocket assembly 28. Notably, each of loop-pocket assemblies 24, 28 can be movably positioned along strap 12 in order to place loop portions 42 of each of assemblies 24, 28 in location to receive the corresponding ends of tightening rod 20. With both ends of rod 20 inserted into loop portions 42 of loop-pocket assemblies 24, 28, rod 20 is reliably fixed in position to hold tourniquet 10 in the twisted, constricting configuration.

Figure 3:
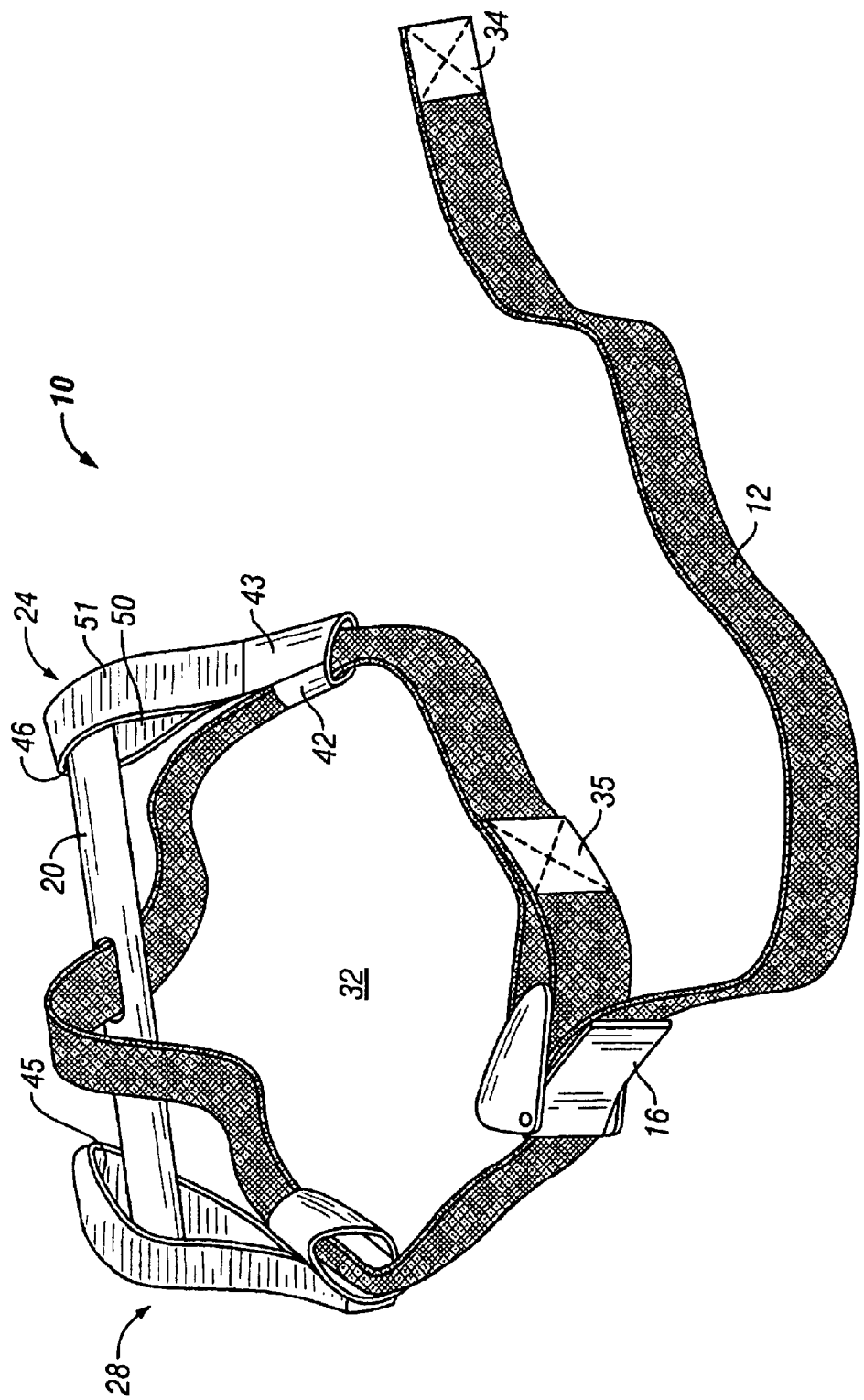
FIG. 3 is a perspective view of the apparatus depicted in FIG. 2, showing both ends of the tightening rod secured in position within retainer pockets of loop-pocket assemblies slidably disposed upon the strap.

In other situations, rod 20 has been used to twist strap 12 to the proper tightness about the patients limb, and rod 20 is in a resultant position roughly perpendicular to tightened strap 12. Reference is made to FIG. 3, where again for the sake of clarity, neither the patent's limb nor the actual twisting of the strap are depicted. End of rod 20 may be inserted into pocket 46 of assembly 24. Rod 20 is fixed in position to secure strap 12 in the appropriately twisted configuration in order to sustain the appropriate constriction upon the treated limb. FIG. 2 shows that the other end of rod 20 can be held similarly within pocket 45 of loop-pocket assembly 28. It is immediately apparent, however, that the invention may function adequately to hold rod 20 fixed and prevent "untwisting," by inserting one end of rod 20 in only one loop portion 42. Notably, each of loop-pocket assemblies 24, 28 can be movably positioned along strap 12 in order to place either of pockets 45, 46 in location to receive corresponding ends of tightening rod 20. With both ends of rod 20 inserted into either pocket 45, 46 rod 20 is fixed in position to hold tourniquet 10 in the appropriate twisted, constricting configuration, even though rod 20 may be perpendicularly oriented in relation to strap 12.

Figure 5:
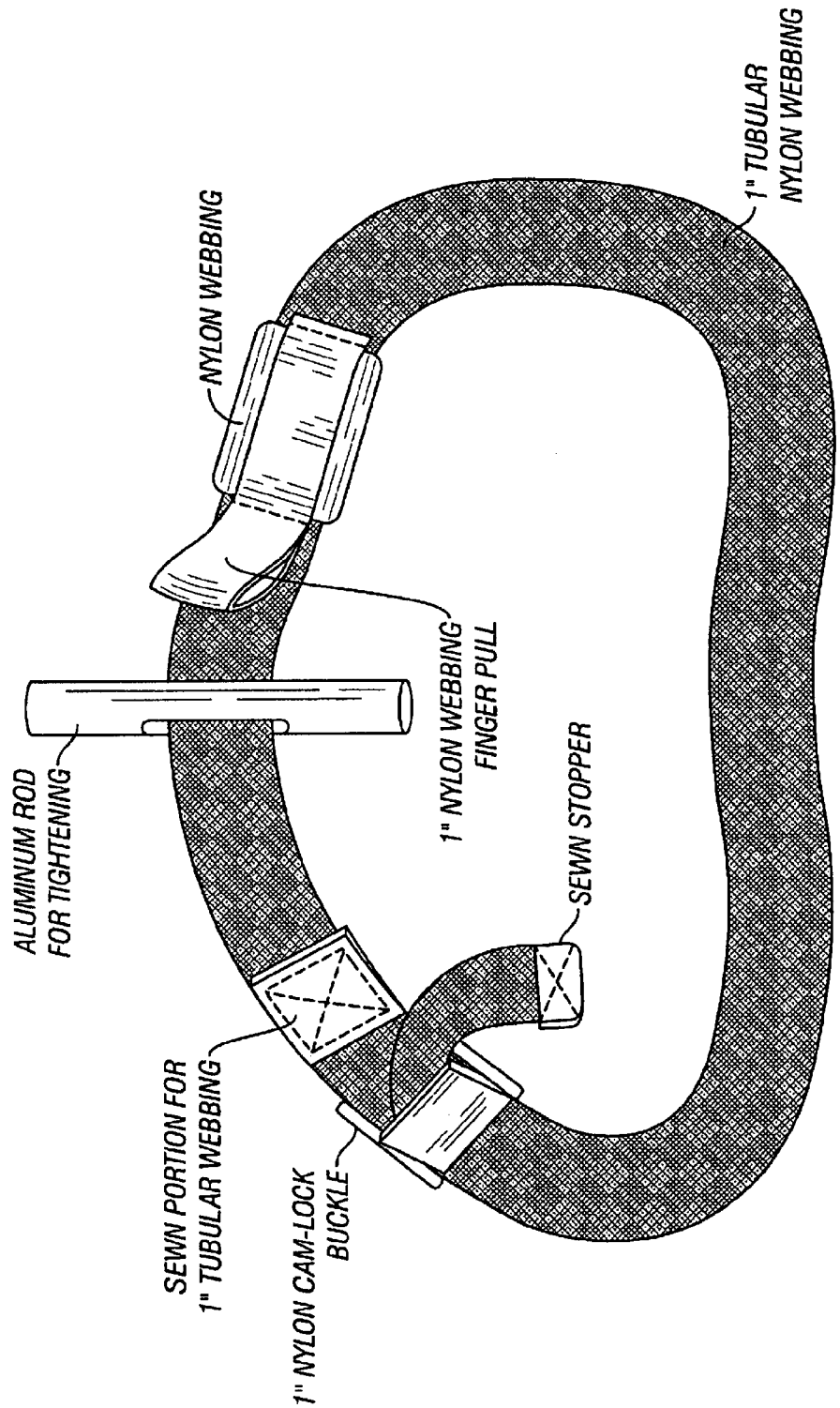
FIG. 5 is a diagram of an alternative embodiment of the tourniquet apparatus of the invention.

FIG. 5 illustrates an alternative embodiment of the invention having single loop assembly 60 that comprises secondary looped finger pull 62 in lieu of any pockets.

Referring to all figures, the method of use preferably involves removing tourniquet 10 from (preferably sterile) storage and disposing the affected limb through opening 32 defined by looped strap 12. Tourniquet 10 is placed in immediate relation "above" the bleeding wound. Tightening rod 20 and loop-pocket assemblies 24, 28 are predisposed upon strap 12, and "free" end 34 of the strap is already threaded through buckle 26, therefore a user has no need to rummage about for tourniquet components losing valuable time. Rather, the tourniquet can be placed rapidly in its proper position, even in unfavorable conditions such as darkness.

With the loop of the tourniquet properly placed upon the affected limb, the user then releases buckle 16 to its "open" position by lifting buckle handle tab 39. Buckle 16 is slipped along strap 12, and free end 34 of strap 10 is pulled, pushing buckle 16 toward the patient's limbs thereby reducing the circumference of the looped portion of strap 12. This tightens strap 12 around the limb. When a preferably trained professional user has determined that strap 12 is adequately tightened by means of sliding buckle 16, the user then forcibly depresses tab 39 to actuate the cam in buckle 16 in a fixed position upon strap 20. The user then accomplishes the actual life-saving constriction of tourniquet 10 by rotating handle-like rod 20 to twist and further tighten strap 12. As strap 12 is twisted about itself, the diameter of opening 32 in the looped portion of strap 12 is further reduced. The twisting action is continued by the user until, in the user's trained opinion, the tourniquet is sufficiently tightened to completely occlude any bleeding. At this point, rod 20 may be approximately perpendicular to strap 12, in which case the user slides loop-pocket assemblies 24, 28 along strap 12 into position on either side of rod 20. The user then lifts either or both pockets 45, 46 over respective ends of rod 20. The ends are tucked securely into pockets 45, 46. Loop-pocket assemblies 24, 28 hold rod 20 in place, preventing its natural counter-rotation and "unwinding" when not fixed in place.

Alternatively, if the proper twisting of strap 12 results in a disposition of rod 20 approximately parallel to the longitude of strap 12, the user slides either or both loop-pocket assemblies 24, 28 to positions adjacent the ends of rod 20, and the ends of rod 20 are tucked into loop portions 42 of assemblies 24, 28. Rod 20 is prevented from "unwinding" as a result. Advantageously, no matter how rod 20 must be positioned to achieve the proper tightening of the tourniquet, loop-pocket assemblies 24, 28 may be used to secure rod 20 against accidental or inadvertent release. Tourniquet 10 therefore remains fixed until deliberately released.

Because each of loop-pocket assemblies 24, 28 has a pair of oppositely-facing pockets 45, 46, the apparatus readily accommodates either clock-wise or counter-clockwise rotation of the rod 20, and versatile placement of either of the pockets over the respective ends of the rod to hold it in place against unwinding, pending the patent's transportation to a critical care facility.

Although the invention has been described in detail with particular reference to these preferred embodiments, other embodiments can achieve the same results. Variations and modifications of the present invention will be obvious to those skilled in the art and it is intended to cover all such modifications and equivalents.

What is claimed is:

1. A tourniquet comprising:
   a strap;
   a fixable buckle, wherein said strap is threadable therethrough;

a rod slidably disposed along said strap, wherein said rod comprises an aperture for receiving said strap there through; and at least one pocket assembly, slidably disposed on said strap, for receiving at least one end of said rod.

2. The tourniquet of claim 1 wherein said strap is comprised of nylon webbing.

3. The tourniquet of claim 1 wherein said strap comprises a length of between approximately 6 inches and approximately 48 inches.

4. The tourniquet of claim 3 wherein said strap comprises a length of between approximately 6 inches and approximately 28 inches.

5. The tourniquet of claim 3 wherein said strap comprises a length between approximately 28 inches and approximately 36 inches.

6. The tourniquet of claim 3 wherein said strap comprise a length of between approximately 36 inches and approximately 48 inches.

7. The tourniquet of claim 1 wherein said buckle comprises a cam-type buckle.

8. The tourniquet of claim 1 wherein said rod comprises a length between approximately 4 inches and approximately 5 inches.

9. The tourniquet of claim 1 wherein said rod is comprised of a material selected from the group consisting of Derin® composite, aluminum, plastic, rubber, wood, and other metal alloys.

10. The tourniquet of claim 1 wherein said pocket assembly is comprised of folded and affixed layers of webbed nylon strap.

11. The tourniquet of claim 10 wherein said pocket assembly defines two oppositely-facing pockets.

12. The tourniquet of claim 1 comprising two pocket assemblies.

13. The method of using the tourniquet as in claim 1 comprising:

removing the tourniquet from its packaging;

disposing an affected limb through an opening defined by a loop formed by
threading the strap through the buckle;

positioning the tourniquet on the limb between a wound and the heart of a patient;

opening the buckle;

sliding the buckle along the strap to reduce the circumference of the opening;

pulling a free end of the strap to reduce the circumference of the opening;

closing the buckle;

rotating the rod to tighten the strap;

sliding the at least one pocket assembly into position alongside the rod; and positioning the ends of the rod within at least one pocket assembly.

* * * * *